(12) United States Patent
McGown et al.

(10) Patent No.: US 9,266,829 B2
(45) Date of Patent: Feb. 23, 2016

(54) QUINONE COMPOUNDS AND THEIR USES FOR THE TREATMENT OF CANCER

(71) Applicant: Onco-NX Limited, Manchester (GB)

(72) Inventors: Alan McGown, Manchester (GB); John Hadfield, Manchester (GB); John Butler, Manchester (GB)

(73) Assignee: Onco-NX Limited, Manchester (GB)

( * ) Notice: Subject to any disclaimer, the term of this patent is extended or adjusted under 35 U.S.C. 154(b) by 0 days.

(21) Appl. No.: 14/418,394

(22) PCT Filed: Jul. 30, 2013

(86) PCT No.: PCT/EP2013/065968
§ 371 (c)(1),
(2) Date: Jan. 29, 2015

(87) PCT Pub. No.: WO2014/020012
PCT Pub. Date: Feb. 6, 2014

(65) Prior Publication Data
US 2015/0210639 A1 Jul. 30, 2015

(30) Foreign Application Priority Data
Jul. 30, 2012 (GB) .................................. 1213486.2

(51) Int. Cl.
| | |
|---|---|
| *C07D 403/10* | (2006.01) |
| *A61K 31/396* | (2006.01) |
| *C07D 203/14* | (2006.01) |
| *A61K 31/337* | (2006.01) |
| *A61K 31/407* | (2006.01) |
| *A61K 33/24* | (2006.01) |

(52) U.S. Cl.
CPC ............ *C07D 203/14* (2013.01); *A61K 31/337* (2013.01); *A61K 31/396* (2013.01); *A61K 31/407* (2013.01); *A61K 33/24* (2013.01); *C07D 403/10* (2013.01)

(58) Field of Classification Search
None
See application file for complete search history.

(56) References Cited

PUBLICATIONS

Danson, et al., Cancer Treatment Reviews, 30:437 (2004).*
Hideo Nakeo et al. "Antileukemic agents. II. new 2, 5-bis(1-aziridinyl)-p-benzoquinone derivatives," *Chemical and Pharmaceutical Bulletin*. vol. 20 (1972) pp. 1968-1979.
Khan P et al. "Development and validation of a sensitive solid-phase extraction and high-performance liquid chromatographic assay for the novel bio-reductive anti-tumor agent RH1 in human and mouse plasma," *Journal of Chromatography B*. vol. 729 (1999): pp. 287-295.
Yoshimoto, Masafumi et al. "Quantitative structure-activity relationships in 2, 5-bis(1-aziridinyl)-p-benzouquinone derivatives against leukemia 1-1210," *Journal of Medicinal Chemistry*. vol. 22. (1979): pp. 491-496.
International Search Report issued in PCT/EP2013/065968 dated Sep. 12, 2013.

* cited by examiner

*Primary Examiner* — Michael Barker
(74) *Attorney, Agent, or Firm* — Mintz Levin Cohn Ferris Glovsky and Popeo, P.C.; Muriel Liberto, Esq.

(57) ABSTRACT

Quinone Compounds and Their Uses for the Treatment of Cancer Quinone compounds having useful therapeutic activity such as anticancer activity, and compositions comprising such compounds, are described. The use of such compounds and compositions in the treatment of cancer is also described.

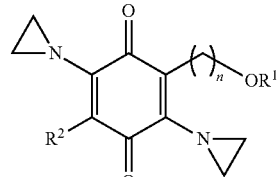

23 Claims, 1 Drawing Sheet

QUINONE COMPOUNDS AND THEIR USES FOR THE TREATMENT OF CANCER

This application is related to United Kingdom patent application GB 1213486.2 filed 30 Jul. 2012, the contents of which are incorporated herein by reference in their entirety.

FIELD OF THE INVENTION

The present invention relates to quinone compounds and their medical uses, in particular for the treatment of cancer. More particularly, the present invention relates to 2,5-diaziridinylbenzoquinone compounds that are pro-drugs capable of activation in cancer cells that express DT-diaphorase.

BACKGROUND OF THE INVENTION

DT-diaphorase (DTD) is an enzyme that is overexpressed in many types of cancerous tissues, including breast, colon, liver, bladder, stomach, the central nervous system (CNS) and lung tumours and in melanomas. Various quinone pro-drugs have been studied to determine their effect on cancer cells expressing DTD. By way of example, the expression of DTD is increased up to 80-fold in primary non-small cell lung cancer (NSCLC) relative to normal lung and up to 400-fold in NSCLC relative to small cell lung cancer (SCLC) cell lines. DTD is also known to activate quinone based pro-drugs and this has been proposed as an approach for selectively targeting cancer cells that express DTD. However, while quinone based pro-drugs have been designed and tested to try and exploit this biology, they have to date been found to suffer from one or more disadvantages.

By way of example, non-small cell lung cancer xenografts with high DTD activity have been shown to be susceptible to the quinone pro-drug mitomycin C. However, although mitomycin C has been shown to have activity in the treatment of non-small cell lung cancer, it is a comparatively poor substrate for DTD (Beall et al., Cancer Research, 54: 3196-3201, 1994) and the metabolism of mitomycin C by DTD is pH-dependent leading to pH-dependent inhibition of DTD at higher pHs (Siegel et al., Mol. Pharmacol., 44:1128-1134, 1993).

Apaziquone or (E)-5-(1-Azirinyl)-3-(hydroxymethyl)-2-(3-hydroxy-1-propenyl)-1-methyl-1H-indole-4,7-dione is an indolequinone that is related to mitomycin C that is also susceptible to reductive conversion to active metabolites by DTD. It has been the subject of clinical trials for the treatment of superficial bladder cancer. However, while Apaziquone is efficiently reduced by DTD, it primarily generates reactive oxygen radicals rather than DNA crosslinks and has been shown to exclusively form DNA strand breaks. Being a conventional "hypoxic-targeting" agent, Apaziquone was not active in spheroid studies demonstrating increased expression of DTD towards the necrotic centre of the spheroid. The results probably relate to the poor ability of Apaziquone to penetrate cells and cross cellular membranes (Bibby et al., Int. J. Oncol., 3: 661-666, 1993).

MeDZQ (2,5-diaziridinyl-3,6-dimethyl-1,4-benzoquinone) is a further example of a promising agent that utilizes the DTD enzyme-directed approach to cancer treatment. Initial results showed that it is more than 150-fold more effective as a substrate for recombinant human DTD than mitomycin C, that it has pH-independent metabolism and did not inactivate DTD at higher pHs (Beall et al., supra; Ross et al. Oncol. Res., 6: 493-500, 1994). Although MeDZQ undergoes bioreductive activation by DTD, it is distinctly different from Apaziquone, as it only produces a very modest increase in cytotoxicity under hypoxic conditions relative to aerobic conditions. Moreover despite displaying a good correlation between DTD activity and MeDZQ cytotoxicity across a range of human tumour cell lines, the formulation of MeDZQ as a useful therapeutic was hampered by its poor solubility.

U.S. Pat. No. 6,156,744 discloses a water soluble quinone pro-drugs, 2,5-diaziridinyl 1-3-(hydroxymethyl)-6-methyl-1, 4-benzoquinone, referred to as "RH1" and its esters formed with acetyl, benzoyl, naphthoyl groups and protected amino acids. U.S. Pat. No. 6,156,744 shows that RH1 is reduced by DTD and selectively kills cells expressing DTD by crosslinking DNA, and that it is more soluble than MeDZQ.

It remains a problem in the art in developing pro-drugs that are activated by DTD and have pharmacological properties to make them effective drug candidates.

SUMMARY OF THE INVENTION

Broadly, the present invention is based on the present inventors' insight that RH1 esters of the prior art tend to be very unstable in aqueous solution, thereby limiting their effectiveness as therapeutic agents. Accordingly, the present invention concerns new quinone-based compounds having improved pharmacological properties that are designed to be selectively activated by 2 electron reduction within tumours. Without wishing to be bound by any particular theory, the present inventors believe that the compounds of the present invention are quinone pro-drugs that undergo an enzymatic 2 electron reduction by DT-diaphorase in cancer cells to produce hydroquinone, a potent DNA cross-linking agent. As DT-diaphorase is over-expressed in a range of human tumours, this means that the compounds of the present invention are selectively cytotoxic to cancer cells as compared to normal cells. Moreover, the present invention further demonstrates that the compounds of the present invention, as represented by the example of the quinone pro-drug Es5, have unexpected stability when compared to other RH1 esters and have greater selectivity towards cells that express DT-diaphorase than prior art compounds such as RH1 and esters thereof. In particular, the ester Es5 (compound 4.65) has a half life of over 24 h, as does its hydrolysis product 4.61, such that it is >20 times more stable than other esters based on RH1.

Broadly, the present invention relates to compounds represented by Formula I:

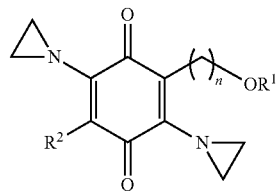

wherein:
n=2, 3, 4, 5, 6 or 7;
$R^1$ is hydrogen, ethanoyl, propanoyl, butanoyl or benzoyl optionally substituted with one or more $C_{1-10}$ alkyl, $C_{1-10}$ alkoxy, hydroxy, halogen, nitro or amino groups; and
$R^2$ is methyl, ethyl or phenyl optionally substituted with one or more $C_{1-10}$ alkyl, $C_{1-10}$ alkoxy, hydroxy, halogen, nitro or amino groups;
and salts and/or solvates thereof, and to methods of treatment using such compounds.

More particularly, the present invention relates to compounds represented by Formula Ia:

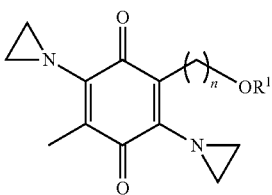

wherein:
n=2, 3 or 4; and
R¹ is hydrogen, ethanoyl, propanoyl or butanoyl; and
salts and/or solvates thereof.

Accordingly, in a first aspect, the present invention provides a compound represented by Formula I:

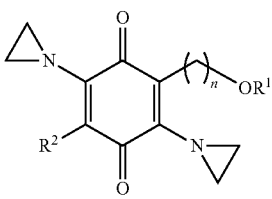

wherein:
n=3, 4, 5, 6 or 7;
R¹ is hydrogen, ethanoyl, propanoyl, butanoyl or benzoyl optionally substituted with one or more $C_{1-10}$ alkyl, $C_{1-10}$ alkoxy, hydroxy, halogen, nitro or amino groups; and
R² is methyl, ethyl or phenyl optionally substituted with one or more $C_{1-10}$ alkyl, $C_{1-10}$ alkoxy, hydroxy, halogen, nitro or amino groups;
or a salt and/or solvate thereof.

In some embodiments, the present invention provides a compound represented by Formula Ia:

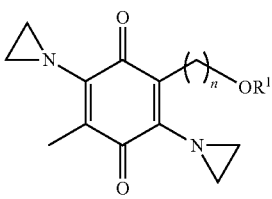

wherein:
n=3 or 4; and
R¹ is hydrogen, ethanoyl, propanoyl or butanoyl; and
salts and/or solvates thereof.

In some preferred embodiments, n=3.

In a preferred embodiment, n=3 and R¹ is hydrogen or ethanoyl, so that the compound is acetic acid 3-(2,5-bis-aziridin-1-yl-4-methyl-3,6-dioxo-cyclohexa-1,4-dienyl)-propyl ester or 2,5-Bisaziridin-1-yl-3-(3-hydroxypropyl)-6-methyl-1,4-benzoquinone, referred to as Es5 and 4-61 in the present application. In any aspect of the present invention, optional halogen substituents may be fluoro, chloro or bromo groups.

In a further aspect, the present invention provides a pharmaceutical composition comprising a compound of Formula I as defined herein, and optionally further comprising one or more further therapeutic agents, for example a further therapeutic agent is for use in treating cancer. Suitable examples may include, not by way of limitation, Cis-platinum (Cis-platin), Docetaxel, cobalt chloride, Epirubicin, Cytarabine (ARA-C), and Mitomycin C. Preferably, the combination of therapeutic agents demonstrates an additive or synergistic effect, more preferably a synergistic effect.

Accordingly, in some embodiments, the present invention provides a pharmaceutical composition comprising a compound of Formula I as defined herein in combination with one or more further therapeutic agents selected from Cis-platinum, Docetaxel, cobalt chloride, and Mitomycin C. Preferably, the composition comprises a compound of Formula I as defined herein in combination with Cis-platinum or cobalt chloride.

Particularly preferred combinations include Es5 (4.65) and Cis-platinum, and Es5 (4.65) and cobalt chloride.

In a further aspect, the present invention provides a compound of Formula I as defined herein, or a pharmaceutical composition comprising a compound of Formula I as defined herein, for use in a method of therapy.

In a further aspect, the present invention provides a compound of Formula I as defined herein, or a pharmaceutical composition comprising a compound of Formula I as defined herein, for use in a method of treating cancer. Preferably, the compounds of the present invention are used for the treatment of types of cancer in which the cancer cells over-express DT-diaphorase. In this case, the compounds of the present invention act as pro-drugs and undergo enzymatic reduction by DT-diaphorase to produce hydroxyquinone, a compound which is cytotoxic to cancer cells. By way of illustration, the present invention may be use in the treatment of brain cancer, leukaemia, non-small cell lung cancer, colon cancer, CNS cancer, melanoma, ovarian cancer, renal cancer, prostate cancer or breast cancer. Accordingly, the present invention may involve determining the suitability of an individual with cancer for treatment with the compounds of the present invention. Preferably, this involves obtaining a sample of cancer cells from a patient, determining whether the cancer cells over-express DT-diaphorase and, if the cancer cells do over-express DT-diaphorase, treating the patient with a compound represented by Formula I. The method may involve the step of assigning the over-expression of DTD to an individual, to determine whether they are suitable, or not, for treatment with a compound represented by Formula I. This may involve the step of assigning the over-expression of DTD on a scale that distinguishes an individual likely to benefit from treatment from an individual who is less likely, or is unlikely, to benefit from treatment, e.g. in some instances the cancer cells from that individual do not express DT-diaphorase at a level that is capable of efficiently reducing a compound of the present invention to a cytotoxic hydroquinone.

In a further aspect, the present invention provides a compound of Formula I as defined herein for use in a method of treating cancer, wherein the method comprises treatment with a further therapeutic agent selected from Cis-platinum, Docetaxel, cobalt chloride, and Mitomycin C. Particularly preferred combinations include Es5 (4.65) and Cis-platinum, Es5 (4.65) and cobalt chloride, Es5 (4.65) and Docetaxel, and Es5 (4.65) and Mitomycin C.

In a further aspect, the present invention provides a method of treating cancer, the method comprising administering a therapeutically effective amount of a compound of Formula I as defined herein, or a pharmaceutical composition comprising a compound of Formula I as defined herein, to a patient in need of treatment thereof.

In a further aspect, the present invention provides a method of treating cancer, the method comprising administering a therapeutically effective amount of a compound of Formula I as defined herein, and a further therapeutic agent selected from cis-platin, Docetaxel, cobalt chloride, and Mitomycin C, to a patient in need of treatment thereof.

The present invention includes the combination of the aspects and preferred features described except where such a combination is clearly impermissible, or is stated to be expressly avoided. Embodiments of the present invention will now be described by way of example and not limitation.

DETAILED DESCRIPTION

DT-Diaphorase

Figure 1:
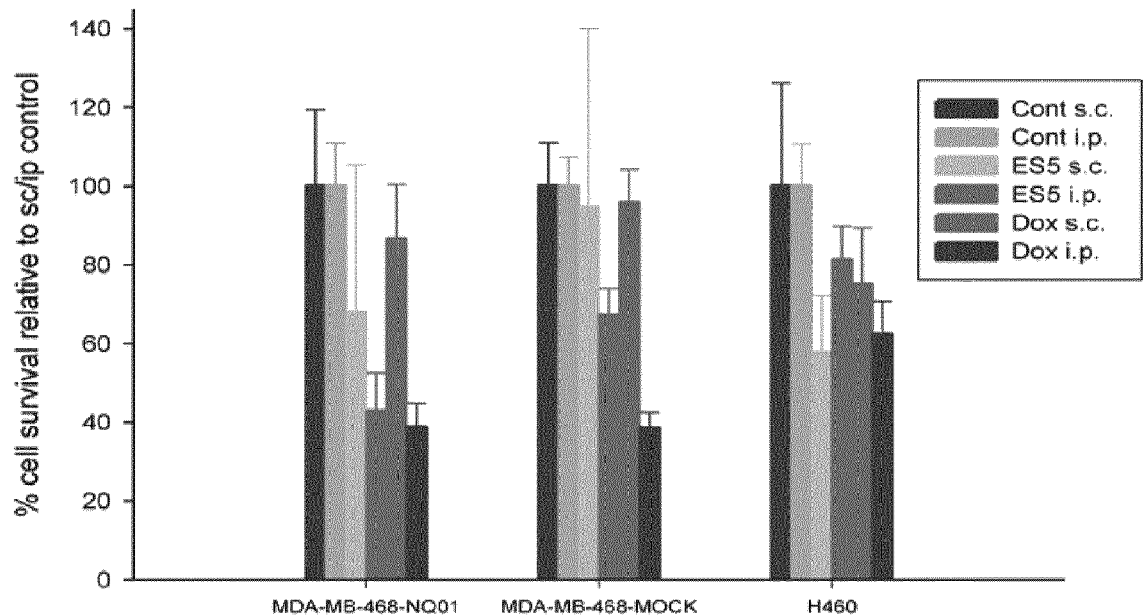
FIG. 1. Graphical representation of the results of the in vivo experiments showing comparison of treatments expressed as S cell survival compared to the relative s.c. or i.p. control.

The compounds, pharmaceutical compositions and medical uses of the present invention are particularly applicable for the treatment of cancers which over-express the enzyme DT-diaphorase (DTD), otherwise known in the art as NQO1 and NAD(P) H: quinone acceptor oxidoreductase 1 (EC 1.6.99.2). Without wishing to be bound by any particular theory, it is generally believed that cancer cells that over-express DTD cause relatively inactive quinone pro-drugs to be selectively activated by an enzymatic 2 electron reduction within the cancer cells to produce hydroquinone which is a potent DNA cross linking agent that is then cytotoxic to the cancer cells. The selectivity of this therapeutic application is achievable because DTD is over-expressed in a range of human tumours as compared to normal cells, including brain cancer, leukaemia, non-small cell lung cancer, colon cancer, CNS cancer, melanoma, ovarian cancer, renal cancer, prostate cancer and breast cancer (Zappa et al., J. Histochem. Cytochem., 49: 1187-1188, 2001; Tudor et al., Anti-Cancer Drugs, 16: 381-391, 2005; Danson et al., Annals of Oncology, 22: 1653-1660, 2011). It is generally preferred that the over-expression of DTD by the cancer cells is the result of the wild-type phenotype of the cells. Alternatively or additionally, the over-expression of DTD may be caused by transforming target cancer cells with nucleic acid encoding DTD (see Danson et al., supra).

However, while this application of the compounds is a preferred aspect of the present invention, it is also known in the art that 2,5-diaziridinylbenzoquinone compounds are cytotoxic to some forms of cancer that do not over-express DTD to any substantial extent, such as leukaemia. It is also known that compounds of this general type may also undergo reduction to form cytotoxic products through the action of other types of reductive enzymes found in cancer cells.

Accordingly, the expression of DTD is a useful tool in the context of the present invention for determining whether a given type of cancer may be treated using the compounds and compositions disclosed herein and/or as a criterion for patient selection for treatment. In both situations, this may involve testing a sample of cancer cells to determine whether DTD is over-expressed, and hence whether the type of cancer or individual patient is likely to benefit from treatment, for example, as demonstrated by Hussein et al., British Journal of Cancer (2009) 101, pp. 55-63.

Accordingly, the present invention includes testing a sample of cancer cells to determine whether a type of cancer or a given individual may be treated in accordance with the present invention. This may be done by determining whether DT-diaphorase protein is present at an elevated level in the cells of the sample, e.g. as compared to expression in normal cells, or by determining the gene expression of DT-diaphorase. The sample may be of cancer cells from the individual. In general over-expression may be determined relative to a control, for example relative to non-cancerous cells, preferably from the same tissue. The method may involve the step of assigning the over-expression of DTD to on a scale that distinguishes an individual likely to benefit from treatment from an individual who is less likely, or is unlikely, to benefit from treatment.

Thus, in one aspect, the present invention includes determining whether a patient has a DT-diaphorase over-expressing cancer can be carried out by analysis of DT-diaphorase protein expression.

Preferably, the presence or amount of DT-diaphorase protein may be determined using a binding agent capable of specifically binding to the DT-diaphorase protein, or fragments thereof. A preferred type of DT-diaphorase protein binding agent is an antibody capable of specifically binding the DT-diaphorase or fragment thereof. The antibody may be labelled to enable it to be detected or capable of detection following reaction with one or more further species, for example using a secondary antibody that is labelled or capable of producing a detectable result, e.g. in an ELISA type assay. As an alternative, a labelled binding agent may be employed in a Western blot to detect DT-diaphorase protein. It is also known that some forms of cancer are characterised by having mutations in the NAD(P)H dehydrogenase [quinone] gene that mean that it encodes functionally inactive DT-diaphorase and this may also be determined as individuals having inactive or reduced levels of DT diaphorase are less likely to respond to treatment with a compound according to the present invention. This can be determined by SNP analysis or restriction fragment length polymorphism (RFLP).

Alternatively, or additionally, the method for determining the presence of DT-diaphorase protein may be carried out on tumour samples, for example using immunohistochemical (IHC) analysis. IHC analysis can be carried out using paraffin fixed samples or frozen tissue samples, and generally involves staining the samples to highlight the presence and location of DT-diaphorase protein.

In one specific example, following the approach used in Zappa et al. (supra) samples of formalin-fixed, paraffin-embedded tissues may be analysed using immunohistochemistry (IHC) to detect DTD expression using anti-DTD monoclonal antibodies(IgG1) derived from a BALB-c mouse immunized with purified recombinant human DTD protein (Siegel et al., Clin. Cancer Res., 4: 2065-2070, 1998). This approach uses non-human-reactive monoclonal mouse antibodies (IgG1) produced in tissue culture were used as negative control reagent. Tissue sections (3 µm) may be deparaffinized in xylene, rehydrated through graded alcohol, and microwaved. Endogenous peroxidase activity and nonspecific binding may be blocked by adding, respectively, peroxidase blocking agent (DAKO EnVision Kit; Carpinteria, Calif.) and 20% normal rabbit serum. Serial sections may be successively incubated with either anti-DTD or control antibodies and then with the secondary antibody (labelled polymer HRP anti-mouse). Immunodetection is performed using a substrate-chromogen solution (hydrogen peroxide and 3,3-diaminobenzidine chromogen). Slides are counterstained with hematoxylin. The intensity of immunostaining (brown staining) was visually scored as 0 (negative), +1 (very weak), +2 (weak), +3 (strong), and +4 (very intense). In this type of assay, there should be substantially no immunostaining in control sections when non-specific antibodies were used (score 0). On the other hand, in cancer cells from cancers or individual patients treatable according to the present invention, it would be expected that the staining in the IHC test would have an intensity of +3 or +4.

In a further example, DTD activity may be determined spectrophotometrically by measuring the reduction of cytochrome c at 550 nm at 25° C., see Chen et al., Biochem J. 284: 855-860, 1992. This assay uses an assay mixture (1 mL) containing 25 mM Tris buffer, pH 7.5, 200 μM NAD(P)H, 0.8 uM menadione and 30 uM cytochrome c. In this assay, menadione is the electron acceptor, and cytochrome c is used to reoxidize the menadiol formed. The effect of other quinone reductases can be distinguished in this assay by the addition of 1 μm dicoumarol, a selective inhibitor of DTD.

Alternatively or additionally, the determination of DT-diaphorase gene expression may involve determining the presence or amount of DT-diaphorase mRNA in a sample. Methods for doing this are well known to the skilled person. By way of example, they include determining the presence of DT-diaphorase mRNA (i) using a labelled probe that is capable of hybridising to the DT-diaphorase nucleic acid, e.g. through the use of techniques such as FISH, and/or (ii) using PCR involving one or more primers based on a DT-diaphorase nucleic acid sequence to determine whether the DT-diaphorase transcript is present in a sample. The probe may also be immobilised as a sequence included in a microarray.

Preferably, detecting DT-diaphorase mRNA is carried out by extracting RNA from a sample of the tumour and measuring DT-diaphorase expression specifically using quantitative real time RT-PCR. Alternatively or additionally, the expression of DT-diaphorase could be assessed using RNA extracted from a tumour sample using microarray analysis, which measures the levels of mRNA for a group of genes using a plurality of probes immobilised on a substrate to form the array.

As mentioned above, the choice of whether protein expression or gene expression, or both, are used to determine DTD over-expression is a decision for the skilled person to make in light of knowledge of the advantages and disadvantages of the different approaches having regards to the respective precision and sensitivity of the techniques, the occurrence of false positives and false negatives and the availability of the different assays for economic or other practical reasons.

Pharmaceutical Compositions

The compounds of the present invention disclosed herein for the treatment of cancer may be administered alone, but it is generally preferable to provide them in pharmaceutical compositions that additionally comprise with one or more pharmaceutically acceptable carriers, adjuvants, excipients, diluents, fillers, buffers, stabilisers, preservatives, lubricants, or other materials well known to those skilled in the art and optionally other therapeutic or prophylactic agents. Examples of components of pharmaceutical compositions are provided in Remington's Pharmaceutical Sciences, 20th Edition, 2000, pub. Lippincott, Williams & Wilkins.

These compounds or derivatives of them may be used in the present invention for the treatment of cancer, in particular cancers that over-express DTD. As used herein "derivatives" of the therapeutic agents includes salts, coordination complexes, esters such as in vivo hydrolysable esters, free acids or bases, hydrates, pro-drugs or lipids, and coupling partners.

Salts of the compounds of the invention are preferably physiologically well tolerated and non toxic. Many examples of salts are known to those skilled in the art. Compounds having acidic groups, such as phosphates or sulphates, can form salts with alkaline or alkaline earth metals such as Na, K, Mg and Ca, and with organic amines such as triethylamine and Tris(2-hydroxyethyl)amine. Salts can be formed between compounds with basic groups, e.g., amines, with inorganic acids such as hydrochloric acid, phosphoric acid or sulphuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques well known in the art.

Derivatives which are pro-drugs of the compounds are convertible in vivo or in vitro into one of the parent compounds. Typically, at least one of the biological activities of the compound will be reduced in the pro-drug form of the compound, and may be activated by conversion of the pro-drug to release the compound or a metabolite of it. The administration of pro-drugs may be advantageous for improving, for example, the storage stability and/or formulation/bio-availability with respect to the parent compound.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor. Coupling partners can be covalently linked to compounds of the invention via an appropriate functional group on the compound such as a hydroxyl group, a carboxyl group or an amino group. Other derivatives include formulating the compounds with liposomes.

The term "pharmaceutically acceptable" as used herein includes compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The active agents disclosed herein for the treatment of DTD over-expressing cancers according to the present invention are preferably for administration to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of the condition being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

The agents disclosed herein for the treatment of DTD over-expressing cancer may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other micro-particulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is in the order of 1 ng/ml to 10 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other micro-particulate systems which are designed to target the active compound to blood components or one or more organs.

Combinations

Compositions comprising agents disclosed herein for the treatment cancer may be used in the methods described herein in combination with standard chemotherapeutic regimes or in conjunction with radiotherapy. Examples of other chemotherapeutic agents include Amsacrine (Amsidine), Bleomycin, Busulfan, Capecitabine (Xeloda), Carboplatin, Carmustine (BCNU), Chlorambucil (Leukeran), Cisplatin (Cis-platinum), Cladribine (Leustat), Clofarabine (Evoltra), cobalt chloride, Crisantaspase (Erwinase), Cyclophosphamide, Cytarabine (ARA-C), Dacarbazine (DTIC), Dactinomycin (Actinomycin D), Daunorubicin, Docetaxel (Taxotere), Doxorubicin, Epirubicin, Etoposide (Vepesid, VP-16), Fludarabine (Fludara), Fluorouracil (5-FU), Gemcitabine (Gemzar), Hydroxyurea (Hydroxycarbamide, Hydrea), Idarubicin (Zavedos). Ifosfamide (Mitoxana), Irinotecan (CPT-11, Campto), Leucovorin (folinic acid), Liposomal doxorubicin (Caelyx, Myocet), Liposomal daunorubicin (DaunoXome®) Lomustine, Melphalan, Mercaptopurine, Mesna, Methotrexate, Mitomycin, Mitoxantrone, Oxaliplatin (Eloxatin), Paclitaxel (Taxol), Pemetrexed (Alimta), Pentostatin (Nipent), Procarbazine, Raltitrexed (Tomudex®), Streptozocin (Zanosar®), Tegafur-uracil (Uftoral), Temozolomide (Temodal), Teniposide (Vumon), Thiotepa, Tioguanine (6-TG) (Lanvis), Topotecan (Hycamtin), Treosulfan, Vinblastine (Velbe), Vincristine (Oncovin), Vindesine (Eldisine) and Vinorelbine (Navelbine). Preferably, the other therapeutic agent is selected to give an additive or synergistic effect.

Also described herein are combination therapy methods, wherein a compound of Formula I as defined herein is used in combination with a further therapeutic agent, preferably a chemotherapeutic agent, to a patient in need of treatment thereof. Accordingly, in a further aspect the present invention provides a method of treating cancer, the method comprising administering a therapeutically effective amount of a compound of Formula I as defined herein, and a further therapeutic agent selected from Cis-platinum, Docetaxel, cobalt chloride, and Mitomycin C, to a patient in need of treatment thereof. The further therapeutic agent may be co-administered or the administration may be sequential. In some preferred embodiments, the further therapeutic agent is Cis-platinum or cobalt chloride. In some preferred embodiments, the second therapeutic agent is Docetaxel or Mitomycin C. Particularly preferred combinations include Es5 (4.65) and Cis-platinum, Es5 (4.65) and cobalt chloride, Es5 (4.65) and Docetaxel, and Es5 (4.65) and Mitomycin C. The cancer may, for example, be brain, leukemia, non-small cell lung cancer, colon cancer, CNS cancer, melanoma, ovarian cancer, renal cancer, prostate cancer or breast cancer.

In some embodiments, cells of the cancer over-express DT-diaphorase. In some embodiments, the compound of Formula I as defined herein undergoes enzymatic reduction by DT-diaphorase to produce hydroxyquinone.

In some embodiments, the method comprises obtaining a sample of cancer cells from a patient, determining whether the cancer cells over-express DT-diaphorase and, if the cancer cells do over-express DT-diaphorase, treating the patient with a compound represented by Formula I and the further therapeutic agent.

In a further aspect, the present invention provides a pharmaceutical composition comprising a compound of Formula I as defined herein, and optionally further comprising one or more further therapeutic agents, for example a further therapeutic agent is for use in treating cancer. Suitable examples may include, not by way of limitation, Cis-platinum, Docetaxel, cobalt chloride, Epirubicin, Cytarabine (ARA-C), and Mitomycin C. Preferably, the combination of therapeutic agents in the composition demonstrates an additive or synergistic effect, more preferably a synergistic effect.

Accordingly, in some embodiments, the present invention provides a pharmaceutical composition comprising a combination of a compound of Formula I as defined herein and one or more further therapeutic agents selected from Cis-platinum, Docetaxel, cobalt chloride, and Mitomycin C. Preferably, the composition comprises a compound of Formula I as defined herein in combination with Cis-platinum or cobalt chloride.

Particularly preferred combinations include Es5 (4.65) and Cis-platinum, and Es5 (4.65) and cobalt chloride.

Accordingly, in a further aspect, the present invention provides a pharmaceutical composition comprising a combination of a compound of Formula I as defined herein and a further therapeutic agent, preferably a further therapeutic agent as defined herein, for use in methods of therapy as described herein.

In one embodiment, the present invention provides a composition comprising Es5 (4.65) and Cis-platinum for use in a method of therapy. In another embodiment, the present invention provides a composition comprising Es5 (4.65) and cobalt chloride for use in a methods of therapy described herein.

Administration

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of approximately 100 μg to approximately 250 mg per kilogram body weight of the subject per day. Where the active compound is a salt, an ester, pro-drug, or the like, the amount administered is calculated on the basis of the parent compound, and so the actual weight to be used is increased proportionately.

EXPERIMENTAL

Materials and Methods

Synthesis of Es5

1,4-Dimethoxy-2-methyl-benzene 2[1]

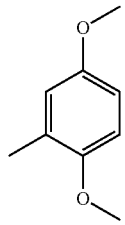

2,5-dimethoxy toluene 1 (9.0 g, 59.21 mmol) in diethyl ether (90 cm$^3$) was added to a stirred solution of iodine monochloride (10.17 g, 62.65 mmol) in chloroform (30 cm) over 30 minutes. The mixture was stirred overnight before 10% sodium thiosulfate (150 cm$^3$) was added. The organics were extracted with 2×75 cm$^3$) of diethyl ether. The organics were combined, washed with saturated aqueous NaHCO$_3$ (150 cm$^3$), brine (100 cm$^3$), dried (MgSO$_4$) and dried under vacuum. The resultant solid was recrystallised from methanol to yield the title compound as red solid 2 (11.3 g, 69%).

R$_f$ 0.52 (SiO$_2$, Hex 3:1 EtOAc).

Mp 80-82° C. (Literature 81-82° C. (Reed et al., JACS, 120(38): 9729-9734, 1998)

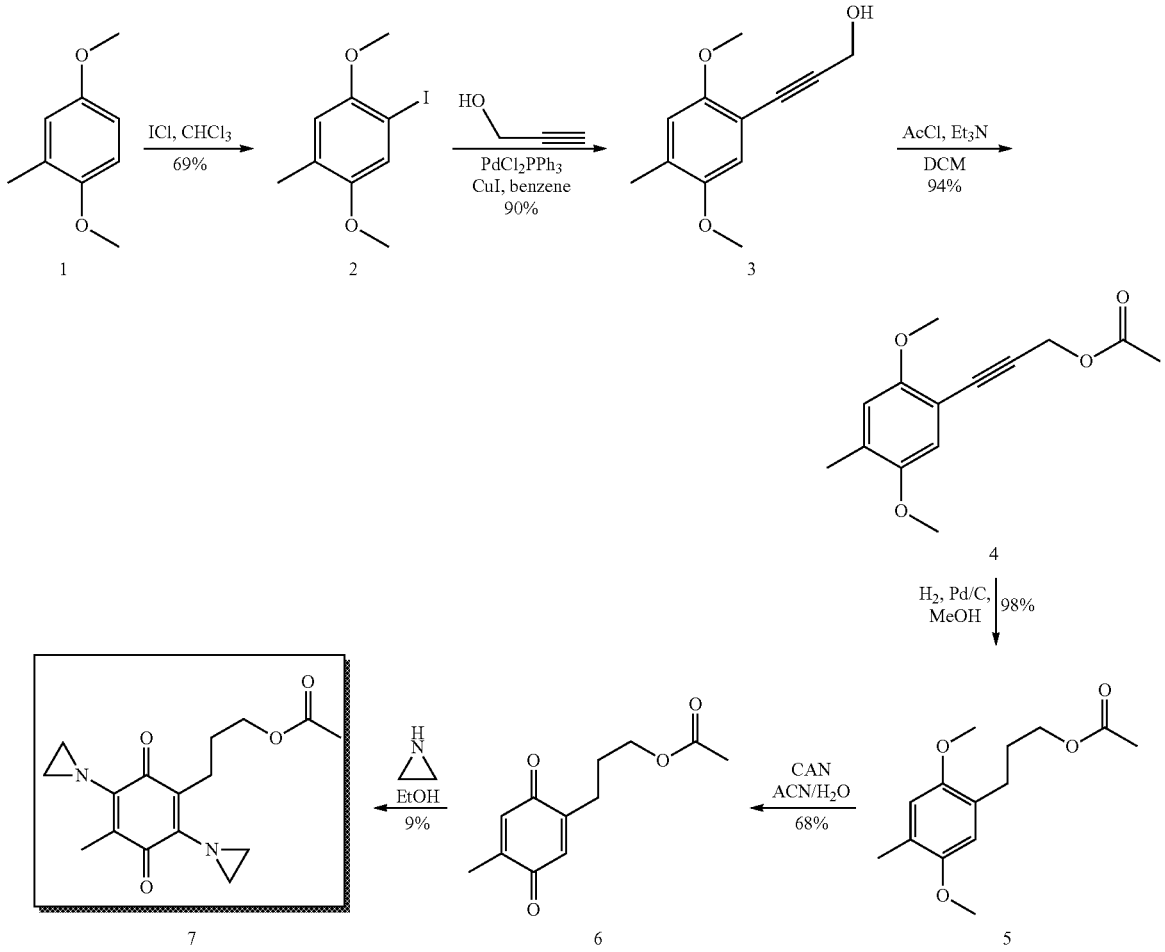

$^1$H NMR (400 MHz, CDCl$_3$) 2.12 (3H, s, CH), 3.72 (3H, s, OCH), 3.75 (3H, s, OCH), 6.60 (1H, s, ArH), 7.10 (1H, s, ArH) ppm.

3-(2,5-Dimethoxy-4-methyl-phenyl)-prop-2-yn-1-ol 3 (Sato, *J. Org. Chem.*, 66(1): 309-314, 2000)

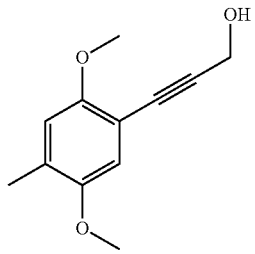

To a flask charged with bis(triphenylphosphine) palladium chloride (151 mg, 0.215 mmol) and copper iodide (273 mg, 1.43 mmol) was added a solution of 1,4-dimethoxy-2-methyl-benzene 2 (2.0 g, 7.20 mmol) in benzene (40 cm). The mixture was cooled to 0° C. before diethylamine (5.19 cm$^3$, 50.35 mmol) and propargyl alcohol (2.1 cm$^3$, 36.0 mmol) was added. The mixture was allowed to stir overnight before being quenched with saturated ammonium chloride (2 cm$^3$) and then concentrated under vaccum. Ethyl acetate was then added (75 cm$^3$) and this was washed with brine (75 cm$^3$), dried (MgSO$_4$) and evaporated under vacuum. Purification was achieved by column chromatography (silica gel, Hex 3:1 EtOAc) to yield the title compound 3 as a pale yellow oil (1.33 g, 90%).

R$_f$ 0.52 (SiO$_2$, Hex 1:1 EtOAc).

$^1$H NMR (400 MHz, CDCl$_3$) 2.15 (3H, s, CH$_3$), 2.55 (1H, br s, OH), 6.68 (3H, s, OCH$_3$), 3.78 (3H, s, OCH$_3$), 4.45 (2H, s, CH$_2$), 6.62 (1H, s, ArH), 6.68 (1H, s, ArH) ppm.

Acetic Acid 3-(2,5-dimethoxy-4-methyl-phenyl)-prop-2-ynyl ester 4

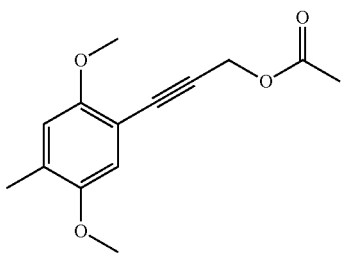 [SMILES: COc1cc(C#CCOC(C)=O)c(OC)cc1C]

To a stirred solution of the alcohol (4.47 g, 21.69 mmol) in dichloromethane (40 cm$^3$) was added triethylamine (4.39 cm$^3$, 43.38 mmol). The mixture was cooled to 0° C. before acetyl chloride (2.55 cm$^3$, 32.48 mmol) was added dropwise. The mixture was allowed to warm to room temperature and stirred overnight. The mixture was quenched with 1M HCl (15 cm$^3$), the organic layer separated and washed with saturated aqueous sodium bicarbonate (30 cm$^3$), brine (30 cm$^3$), dried (MgSO$_4$) and evaporated under vacuum to yield the title compound a yellow oil 4 (5.08 g, 94%).

R$_f$ 0.61 (SiO$_2$, Hex 1:1 EtOAc).

$^1$H NMR (400 MHz, CDCl$_3$) 2.08 (3H, s, CH$_3$), 2.18 (3H, s, CH$_3$), 3.72 (3H, s, OCH$_3$), 3.80 (3H, s, OCH$_3$), 4.90 (2H, s, CH$_2$), 6.62 (1H, s, ArH), 6.78 (1H, s, ArH) ppm.

Acetic Acid 3-(2,5-dimethoxy-4-methyl-phenyl)-propyl ester 5

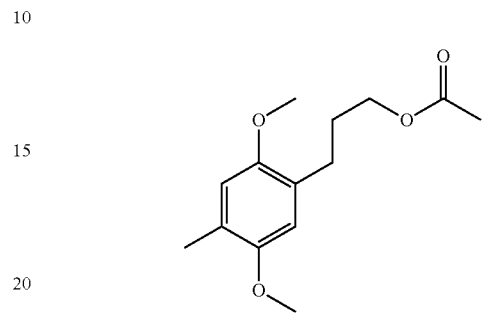

The alkyne 3 (5.01 g, 20.2 mmol) was dissolved in methanol (100 cm$^3$) and Pd/C (100 mg) was added. The reaction flask was purged with hydrogen gas and stirred overnight. The reaction mixture was filtered through celite and the solvent removed under vacuum to yield the title compound 5 as a brown oil (4.98 g, 98%).

R$_f$ 0.36 (SiO$_2$, Hex 1:1 EtOAc).

$^1$H NMR (400 MHz, CDCl$_3$) 1.98 (2H, m. CH$_2$), 2.10 (3H, s, CH), 2.24 (3H, s, CH$_3$), 2.68 (2H, m, CH$_2$), 3.82 (3H, s, OCH$_3$), 3.86 (3H, s, OCH$_3$), 4.15 (2H, m, CH$_2$), 6.66 (1H, s, ArH), 6.70 (1H, s, ArH) ppm.

$^{13}$C NMR (400 MHz, CDCl$_3$) 14.1, 16.1, 21.0, 26.7, 28.9, 32.3, 55.9, 56.1, 64.3, 112.8, 113.8, 124.9, 127.4, 151.2, 151.4, 171.22.

Acetic Acid 3-(4-methyl-3,6-dioxo-cyclohexa-1,4-dienyl)-propyl ester 6

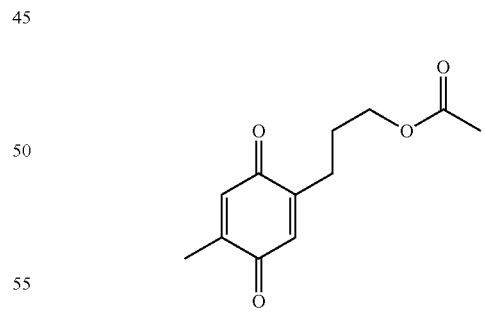

To a solution of 5 (1.26 g, 4.99 mmol) in acetonitrile (15 cm$^3$) was added ceric ammonium nitrate (5.50 g, 9.99 mmol) in water (10 cm$^3$) dropwise. The mixture was stirred for 1 hr before the organics were extracted with dichloromethane (3×25 cm$^3$), washed with brine (25 cm$^3$), dried (MgSO$_4$) and concentrated under vacuum to yield the title compound as a brown oil 6 (756 mg, 68%).

R$_f$ 0.69 (SiO$_2$, Hex 1:1 EtOAc).

$^1$H NMR (400 MHz, CDCl$_3$)

Acetic Acid 3-(2,5-bis-aziridin-1-yl-4-methyl-3,6-dioxo-cyclohexa-1,4-dienyl)-propyl ester 7

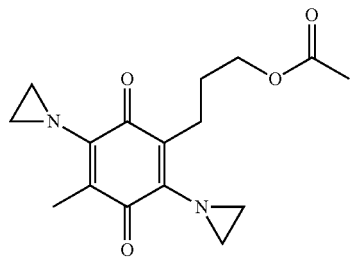 [SMILES: CC(=O)OCCCC1=C(N2CC2)C(=O)C(C)=C(N2CC2)C1=O]

Quinone 6 (756 mg, 3.40 mmol) was dissolved in ethanol (15 cm³), cooled to 0° C. and aziridine (0.50 cm³, 11.6 mmol) was added dropwise. The mixture was stirred for 1 hr at 0° C. and then left in the fridge for 72 hr. The solvent was removed under vacuum. The red solid was triturated with diethyl ether and dried. The red solid was further purified by column chromatography (silica gel, Hex 1:1 EtOAc) to yield the title compound 7 as a red solid (98 mg, 9%).

$R_f$ 0.52 (SiO$_2$, Hex 1:1 EtOAc).

$^1$H NMR (400 MHz, CDCl$_3$)

Synthesis of Comparative Compounds

RH1, MeDZQ and all of the esters were synthesized according to prior art protocols (Kidscan laboratories) and were made up as 10 mM stock solutions in DMSO for testing. Table 1 show the structures and of some esters and their half life in Tris buffer in addition to their IC$_{50}$ values on MDA 468 and MDA NQ01 cell lines.

Stability Testing

The stability of esters and their hydrolysis products was measured in solution. (50 μM Es5 in Tris buffer (0.1 mol dm$^{-3}$) at pH 7.4). Samples were taken at timed intervals up to 24 hours and analysed by HPLC. The detection wavelength was 330 nm. Chromatographic analysis was carried out by isocratic elution with 30:70 MeOH: Tris buffer (0.1 mol dm$^{-3}$, pH 7.4), at 1 ml min$^{-1}$. The chromatographic separation of the drug was achieved using a Hypersil ODS column with 250 mm×4.6 mm I.D.

TABLE 1

The structures of the RH1 esters and their half life values.

| Compound | RH1 Esters and ester hydrolysis products. Chemical structures | $T_{1/2}$ in buffer pH 7.0 |
|---|---|---|
| 4-05 | | <10 minutes |
| 4-07 | | <20 minutes |
| 4-09 | | <30 minutes |
| 4-10 | | <30 minutes |

TABLE 1-continued

The structures of the RH1 esters and their half life values.

| Compound | RH1 Esters and ester hydrolysis products. Chemical structures | $T_{1/2}$ in buffer pH 7.0 |
|---|---|---|
| 4-11 | | <30 minutes |
| 4-14 | | <30 minutes |
| 4-20 | | 20 minutes |
| 4-36 | | <30 minutes |
| 4-38 | | 20 minutes |
| 4-39 | | <30 minutes |
| 4-61 | | >24 hours |

TABLE 1-continued

The structures of the RH1 esters and their half life values.

| Compound | RH1 Esters and ester hydrolysis products. Chemical structures | $T_{1/2}$ in buffer pH 7.0 |
|---|---|---|
| 4-65 (Es5) | | >24 hours |
| 4-70 | | <60 minutes |
| 4-71 | | <60 minutes |

Selectivity Testing

Compounds of the present invention such as Es5 and 4-61 show excellent selectivity towards cells that express DT-diaphorase. Selectivity was found to exceed that shown by RH1. $IC_{50}$ values measured using an MTT assay.

Table 2 shows a summary of the $IC_{50}$ values for numerous drugs tested in MDA483 and NQ01 cells. The data demonstrate that Es5 shows excellent selectivity towards cells that express DT-diaphorase when compared to other anti-cancer agents. By way of comparison, the MDA468 to NQ01 differential for Es5 is >80 fold, compared to ~5 fold for Mitomycin C and >30 fold for RH1. The hydrolysis product 4-61 of Es5 also shows excellent selectivity, having $IC_{50}$ values of 0.41 nM on MDA NQO1 and 16.97 nM on MDA 468, and consequently a DT diaphorase enhancement ratio of 41.

TABLE 2

The effect of Es5 (4.65) and other anti-cancer agents on MDA468 and NQ01 cells.

| RH1 Esters | $IC_{50}$ on MDA468 | $IC_{50}$ on NQ01 |
|---|---|---|
| RH1 | 4.41 nM | 120 pM |
| Es5 (4.65) | 25 nM | 230 pM |
| Cisplatin | 675 nM | 570 nM |
| Docetaxel | 1.15 nM | 1.88 nM |
| Mitomycin C | 50 nM | 10 nM |
| 5-fluorouracil | 7.96 µM | 12 µM |
| Epirubicin | 23.2 nM | 27.5 nM |
| Methotrexate | 45 nM | 27 nM |
| Cobalt chloride | 35 µM | 54 µM |
| Vinblastine | 16 nM | 18.3 nM |
| Cytosine arabinoside (ARA-C) | 250 nM | 240 nM |

Activation of Es5

The cleavage of Es5 by esterase and cell extracts and its activation were investigated. Es5 is stable in aqueous buffers, but underwent a slow hydrolysis in serum ($t_{1/2}$=100 mins). Experiments with porcine esterase showed that it rapidly cleaved Es5 to its hydrolysis product, a result that was repeated when porcine brain extracts were used. Cell extracts from the DT-diaphorase expressing MDA468 NQ01 cell line rapidly cleaved the ester, whereas an extract from the DT-diaphorase null MDA 468 cell line did so at a much reduced rate, indicating that activation is likely to be greater in DT-diaphorase expressing cells or tumours.

As mentioned above, most RH1 esters were very unstable in aqueous solution and hydrolysed to RH1 within 30 minutes. The rates were such that the kinetics could not be determined by HPLC. Es5 was much more stable as shown in the tables above.

The stability profile of Es5 was measured in Tris buffer (0.1 mol dm$^{-3}$, pH 7.0), RPMI media (pH 7.0) and serum at room temperature and showed the loss of Es5, concurrent with a gain of the alcohol 4.61 in serum over the same time scale.

Cell Lysate Esterase Reaction

The degradation of Es5 by esterases from cell lysate of the two cell lines MDA NQ01 and MDA468 was investigated. Es5 was unstable in the MDA NQ01 cell line extract and degraded to the alcohol 4.61 displayed a half-life of approximately 160 minutes at room temperature. In the DTD-null cell line MDA468, degradation of the parent molecule to its alcohol was at an appreciably lower rate.

Apoptosis

Based on the method described in Martin et al. (*Journal of Experimental Medicine*. 182, 1545-1556. 1995), the induction of apoptosis caused by the compounds of the present invention was determined. Apoptosis, as measured by Annexin V binding, showed the induction of programmed cell death occurs within 2 hours in the DT-diaphorase expressing cells, whereas no death is seen at this time in the DT-diaphorase null MDA 468 cells. A reduced level of apoptosis is seen in this cell line after 4 hrs. This shows the differential effect of Es5 on DT-diaphorase expressing and non-expressing cells.

DNA Damage

DNA damage was measured using the Comet assay to investigate the effect of Es5 on the comet head and tail intensities following treatment of MDA468NQ01 and the DT-diaphorase null MDA468 cell lines. These experiments showed for both cell lines that the addition of $H_2O_2$ causes DNA strand breaks resulting in an increased accumulation of DNA in the tail compared to the head. In the DT-diaphorase expressing cell line (NQ01) treatment with 10 nM Es5 for 2 hrs increased the proportion of DNA in the head compared to treatment with $H_2O_2$ alone. This showed that the DNA has been cross-linked by Es5. In the DT-diaphorase deficient cell line treatment with Es5 did not reduce tail intensity showing that in the absence of activation by DT-diaphorase Es5 is not a DNA cross-linking agent, this being the proposed mechanism of action of Es5. Following 6 hours of incubation there was evidence of cross-linking in the DT-diaphorase null cell line. Without wishing to be bound by any particular theory, the inventors believe that this must arise by a different mechanism such as 2×one electron reductions, rather than the 2 electron reduction that occurs with DT-diaphorase.

Comparison of Es5 and RH1

Table 3 shows a comparison of the characteristics of Es5 (4.65) with RH1 and provides their combination indices with Cis-platinum, Docetaxel, cobalt chloride, Epirubicin, ara-C, and Mitomycin C. For comparison, the combination index at $IC_{50}$ of MMC and cobalt chloride is 0.443 in MDA468 and 0.239 in NQ01 cells. As can be seen from Table 3, the combination of Es5 and Cis-platinum demonstrates synergy in both cell lines, while the combination of Es5 and cobalt chloride demonstrates strong synergy in both cell lines. A combination of Es5 and Docetaxel shows an additive effect with respect to NQ01, while showing a moderately inhibitory effect with respect to MDA468, while a combination of Es5 and Mitomycin C shows an additive effect with respect to NQ01 and a slight antagonism with respect to MDA468.

TABLE 3

A comparison of the characteristics of Es5 and RH1, and their combination indices with some other anti-cancer agents. $T_{90}$ = time taken to degrade to 90% of starting concentration.

| Characteristic | RH1 | Es5 (4.65) |
|---|---|---|
| Solubility (aqueous) | 500 μg/ml (water) | 150 μg/ml (PBS) |
| Stability (aqueous) | >7 days | >7 days |
| Solubility (organic) | >30 mg/ml (DMSO/chloroform) | 9.4 mg/ml (ethanol) |
| Stability (organic) | months | >1 month |
| Detection limits by HPLC (330 nm) | <50 pmoles | <50 pmoles |
| Degradation by serum esterase | NA | $t_{90}$ 90 mins |
| Degradation by porcine liver esterase | NA | $t_{1/2}$ 1 min |
| Degradation by MDA468 cell extract | NA | $t_{1/2}$ 280 mins (19.6 nmoles/hr/$10^6$ cells) |
| Degradation by MDA NQ01 cell extract | NA | $t_{1/2}$ 160 mins (11.25 nmoles/hr/$10^6$ cells) |
| $IC_{50}$ MDA468 | 3.5 nM | 20-25 nM |
| $IC_{50}$ MDA NQ01 | 120 pM | 230 pM |
| Combination index at $IC_{50}$ with Cis-platinum in MDA468 | 0.499 (synergy) | 0.567 (synergy) |
| Combination index at $IC_{50}$ with Cis-platinum in MDA NQ01 | 0.672 (synergy) | 0.674 (synergy) |
| Combination index at $IC_{50}$ with Docetaxel in MDA468 cells | 0.850 (slight synergy)) | 1.387 (moderately inhibitory) |
| Combination index at $IC_{50}$ with Docetaxel in NQ01 cells | 0.864 (slight synergy) | 0.964 (additive) |
| Combination index at $IC_{50}$ with cobalt chloride in MDA468 cells | 0.170 (strong synergy) | 0.464 (strong synergy) |
| Combination index at $IC_{50}$ with cobalt chloride in NQ01 cells | 0.80 (moderate synergy) | 0.54 (strong synergy) |
| Combination index at $IC_{50}$ with Epirubicin in MDA468 cells | 4.81 (strong antagonism) | 1.49 (antagonism) |
| Combination index at $IC_{50}$ with Epirubicin in NQ01 cells | 2.09 (antagonism) | 2.04 (antagonism) |
| Combination index at $IC_{50}$ with ARC-C in MDA468 cells | 1.45 (slight antagonism) | 1.2 (slight antagonism) |
| Combination index at $IC_{50}$ with ARA-C in NQ01 cells | 1.22 (slight antagonism) | 1.22 (slight antagonism) |
| Combination Index at $IC_{50}$ with Mitomycin C in MDA468 cells | 0.577 (synergy) | 1.4 (slight antagonism) |
| Combination Index at $IC_{50}$ with Mitomycin C in NQ01 cells | 1.2 (slight antagonism) | 0.924 (additive) |
| pH stability | $t_{1/2}$ = 0.96 days at pH 9.82 | $t_{1/2}$ >6 days at pH 9.44 |
| | $t_{1/2}$ = 43.52 days at pH 7.33 | $t_{1/2}$ >6 days at pH 7.44 |
| | $t_{1/2}$ = 4.46 days at pH 5.95 | $t_{1/2}$ >6 days at pH 6.2 |

TABLE 3-continued

A comparison of the characteristics of Es5 and RH1, and their combination indices with some other anti-cancer agents. $T_{90}$ = time taken to degrade to 90% of starting concentration.

| Characteristic | RH1 | Es5 (4.65) |
|---|---|---|
|  | $t_{1/2}$ = 4.36 days at pH 5.95 | $t_{1/2}$ >6 days at pH 5.9 |
|  | $t_{1/2}$ = 0.07 days at pH 4.16 | $t_{1/2}$ = 2.4 days at pH 4.35 |
|  | $t_{1/2}$ = 0.07 days at pH 4.16 (nearest comparison from AAPS PharmSciTech 2007; 8 (1) Article 16) | $t_{1/2}$ = 1 day at pH 3.9 |
| Temperature stability | 4 C. $t_{90}$ >7 days | 4 C. $t_{90}$ >6 days |
|  | Ambient $t_{90}$ 3 days | Ambient $t_{90}$ 4 days |
|  | 40 C. $t_{90}$ 2 days | 37 C. $t_{90}$ 4 days |
|  | 55 C. $t_{1/2}$ 2 days | 55 C. $t_{1/2}$ <1 day |

Efficacy of Es5 In Vivo

The activity of Es5 (4.65) was evaluated in vivo against 3 cancer cell lines H460, MDA-MB-468-NQ01 and MDA-MB-468-MOCK using the in vivo hollow fibre assay (HFA), with fibres implanted at both intraperitoneal (i.p.) and subcutaneous (s.c.) sites. Es5 and the control agent Doxorubicin were administered as multiple doses by intraperitoneal injection (i.p.) on days 3, 4, 5 & 6 at 0.5 mg/kg/day and 2.5 mg/kg/day respectively.

Es5 (4.65) demonstrated significant efficacy (p<0.01) in terms of cell survival compared to the untreated control in all 3 cell lines where the fibres were implanted at the i.p. site, and in H460 where the fibres were implanted at the s.c. site. These results were similar to the standard control agent Doxorubicin indicating that this compound has potential as an anti-cancer agent.

Material and Methods

Es5 (4.65) was dissolved in saline solution with the aid of some vortexing.

Cell Lines.

Three human tumour cell lines were selected for analysis: H460 NSCLC (from ICT) and two breast carcinoma lines MDA-MB-468-NQ01 and MDA-MB-468-MOCK (both supplied by Onco-NX). Cells were cultured in RPMI 1640 cell culture medium supplemented with 1 mM sodium pyruvate, 2 mM L-glutamine and 10% foetal bovine serum (all from Sigma), and maintained as monolayer cultures at 37° C. in a humidified 5% $CO_2$ environment.

Animals.

Female Balb/C immunodeficient nude mice aged 6-8 weeks were used (Harlan UK, Blackthorn, UK). Mice were kept in cages housed in isolation cabinets in an air-conditioned room with regular alternating cycles of light and darkness. They received Teklad 2018 diet (Harlan, Blackthorn, UK) and water ad libitum. All animal procedures were carried out under a project licence issued by the UK Home Office and UKCCCR guidelines were followed throughout.

Hollow Fibre Assay.

Cells were loaded into sterilised colour-coded PVDF Spectra/Por hollow fibres (HF) (Spectrum Medical Inc, Houston, Tex., USA). Briefly cells were harvested and resuspended in cell culture medium at the required cell density. This preparation was then loaded into the HF and the ends were clamped and heat-sealed. The HF was then cut into 1.5 cm lengths which were again heat-sealed at both ends, and then transferred to 6-well plates containing medium before implantation for the in vivo experiments, or were incubated at 37° C. in a humidified 5% $CO_2$ environment for varying times before processing using the modified MTT assay as described below.

For the in vivo experiments, under brief inhalation anaesthesia (2% isoflurane), one loaded hollow fibre for each of the cell lines was transplanted intraperitoneally or subcutaneously on the dorsal flank of each mouse and the mice were allowed to recover. Each group consisted of 6 mice and the implantation day was termed 'day 0'.

For assessment of the therapeutic response of Es5 (4.65), on days 3, 4, 5 & 6 mice were treated with Es5 (4.65) at 0.5 mg/kg/day or Doxorubicin at 2.5 mg/kg/day.

Mice were sacrificed on day 7 post-implantation, fibres removed, and cell survival analysed using a modified MTT assay, comparing absorbances seen for the treated groups with the corresponding untreated control group. Statistical analysis was carried out using a Student's t-test.

Results

Figure 2:
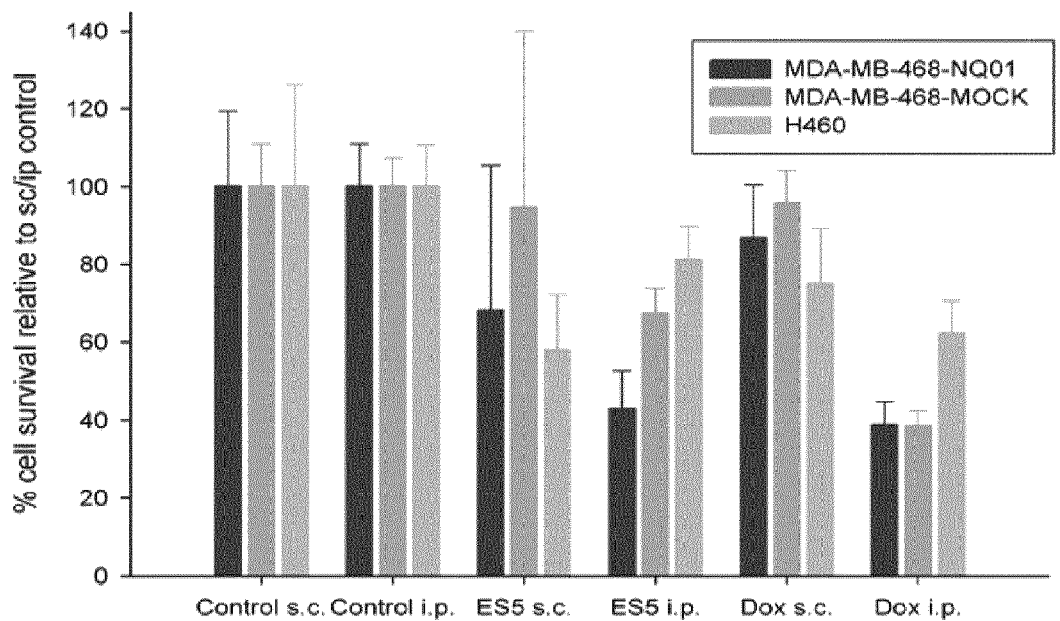
FIG. 2. Graphical representation of the results of the in vivo experiments showing comparison of cell lines expressed as % cell survival compared to the relative s.c. or i.p. control.

FIGS. 1 and 2 show the results obtained for the study, with the data expressed as percentage cell survival compared to the relative s.c. or i.p. untreated control. FIG. 1 presents the data grouped for each cell line, whereas in FIG. 2 this is presented for each treatment.

Es5 demonstrated significant efficacy (p<0.01) in terms of cell survival compared to the untreated control in all 3 cell lines where the fibres were implanted at the i.p. site, and in H460 where the fibres were implanted at the s.c. site. These results were similar to the standard control agent Doxorubicin, although this agent did not demonstrate significant efficacy against any of the cell lines at the s.c. site.

Es5 also demonstrated improved efficacy in the NQ01-expressing compared to the Mock MDA-MB-468 cell line, whereas there was little difference seen for Doxorubicin.

The documents disclosed herein are all expressly incorporated by reference in their entirety.

The invention claimed is:

1. A compound represented by Formula I:

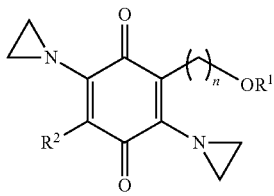

wherein:
n=3, 4, 5, 6 or 7;
$R^1$ is hydrogen, ethanoyl, propanoyl, butanoyl or benzoyl optionally substituted with one or more $C_{1-10}$ alkyl, $C_{1-10}$ alkoxy, hydroxy, halogen, nitro or amino groups; and
R is methyl, ethyl or phenyl optionally substituted with one or more $C_{1-10}$ alkyl, $C_{1-10}$ alkoxy, hydroxy, halogen, nitro or amino groups;
or a salt and/or solvate thereof.

2. The compound of claim 1 which is represented by Formula 1a:

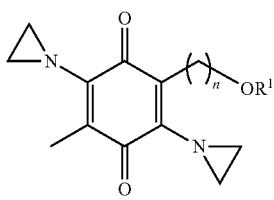

wherein:
n=3 or 4; and
$R^1$ is hydrogen, ethanoyl, propanoyl or butanoyl; and
salts and/or solvates thereof.

3. The compound of claim 2, wherein n=3.

4. The compound of claim 2, wherein $R^1$ is hydrogen or ethanoyl.

5. The compound of claim 2, which is acetic acid 3-(2,5-bis-aziridin-1-yl-4-methyl-3,6-dioxo-cyclohexa-1,4-dienyl)-propyl ester or 2,5-Bisaziridin-1-yl-3-(3-hydroxypropyl)-6-methyl-1,4-benzoquinone, or a salt and/or solvate thereof.

6. A pharmaceutical composition comprising a compound according to claim 2.

7. The pharmaceutical composition of claim 6, further comprising one or more further therapeutic agents.

8. The pharmaceutical composition of claim 7, wherein the further therapeutic agent is for use in treating cancer.

9. The pharmaceutical composition of claim 8, wherein the further therapeutic agent is selected from Cis-platinum, Docetaxel, and Mitomycin C.

10. The pharmaceutical composition of claim 9, wherein the further therapeutic agent is Cis-platinum.

11. The pharmaceutical composition of claim 9, wherein the further therapeutic agent is Docetaxel or Mitomycin C.

12. A method of treating cancer, the method comprising administering a therapeutically effective amount of the compound of claim 1, or the composition of claim 6, to a patient in need of treatment thereof.

13. The method of treating cancer according to claim 12, wherein cells of the cancer over-express DT-diaphorase.

14. The method of treating cancer according to claim 12, wherein the compound undergoes enzymatic reduction by DT-diaphorase to produce hydroxyquinone.

15. The method of treating cancer according to claim 12, wherein the cancer is brain cancer, leukemia, non-small cell lung cancer, colon cancer, CNS cancer, melanoma, ovarian cancer, renal cancer, prostate cancer or breast cancer.

16. The method of treating cancer according to claim 12, wherein the method comprises obtaining a sample of cancer cells from a patient, determining whether the cancer cells over-express DT-diaphorase and, if the cancer cells do over-express DT-diaphorase, treating the patient with a compound represented by Formula I.

17. A method of treating cancer, the method comprising administering a therapeutically effective amount of:
a compound of claim 1, and
a further therapeutic agent selected from Cis-platinum, Docetaxel, and Mitomycin C, to a patient in need of treatment thereof.

18. The method of treating cancer according to claim 17, wherein the further therapeutic agent is Cis-platinum.

19. The method of treating cancer according to claim 17, wherein the further therapeutic agent is Docetaxel or Mitomycin C.

20. The method of treating cancer according to claim 17, wherein cells of the cancer over-express DT-diaphorase.

21. The method of treating cancer according to claim 17, wherein the compound undergoes enzymatic reduction by DT-diaphorase to produce hydroxyquinone.

22. The method of treating cancer according to claim 17, wherein the cancer is brain, leukemia, non-small cell lung cancer, colon cancer, CNS cancer, melanoma, ovarian cancer, renal cancer, prostate cancer or breast cancer.

23. The method of treating cancer according to claim 17, wherein the method comprises obtaining a sample of cancer cells from a patient, determining whether the cancer cells over-express DT-diaphorase and, if the cancer cells do over-express DT-diaphorase, treating the patient with a compound represented by Formula I and the further therapeutic agent.

* * * * *